US012617821B2

(12) United States Patent  
Kelsic et al.

(10) Patent No.: US 12,617,821 B2  
(45) Date of Patent: *May 5, 2026

(54) ENGINEERED VIRAL CAPSID POLYPEPTIDES AND USES THEREOF

(71) Applicant: PRESIDENT AND FELLOWS OF HARVARD COLLEGE, Cambridge, MA (US)

(72) Inventors: Eric Kelsic, Cambridge, MA (US); Sam Sinai, Somerville, MA (US); Pierce Ogden, Somerville, MA (US); George M. Church, Brookline, MA (US)

(73) Assignee: PRESIDENT AND FELLOWS OF HARVARD COLLEGE;

( * ) Notice: Subject to any disclaimer, the term of this patent is extended or adjusted under 35 U.S.C. 154(b) by 800 days.

This patent is subject to a terminal disclaimer.

(21) Appl. No.: 17/774,306

(22) PCT Filed: Nov. 6, 2020

(86) PCT No.: PCT/US2020/059294  
§ 371 (c)(1),  
(2) Date: May 4, 2022

(87) PCT Pub. No.: WO2021/092298  
PCT Pub. Date: May 14, 2021

(65) Prior Publication Data

US 2023/0002451 A1  Jan. 5, 2023

Related U.S. Application Data

(60) Provisional application No. 62/932,646, filed on Nov. 8, 2019.

(51) Int. Cl.  
*C07K 14/075* (2006.01)  
*C12N 15/861* (2006.01)

(52) U.S. Cl.  
CPC .......... *C07K 14/075* (2013.01); *C12N 15/861* (2013.01); *C12N 2750/14122* (2013.01); *C12N 2750/14143* (2013.01)

(58) Field of Classification Search  
CPC ............... C07K 14/075; C12N 15/861; C12N 2750/14122; C12N 2750/14143  
See application file for complete search history.

(56) References Cited

U.S. PATENT DOCUMENTS

| | | | |
|---|---|---|---|
| 6,156,303 A | 12/2000 | Russell et al. | |
| 9,233,131 B2 * | 1/2016 | Schaffer | C07K 14/005 |
| 9,441,244 B2 * | 9/2016 | Schaffer | A61P 31/12 |
| 2009/0215879 A1 | 8/2009 | Diprimio et al. | |
| 2014/0050701 A1 | 2/2014 | Zhong et al. | |
| 2014/0341852 A1 | 11/2014 | Srivastava et al. | |
| 2017/0096683 A1 | 4/2017 | Scaria et al. | |
| 2022/0396808 A1 | 12/2022 | Kelsic | |

FOREIGN PATENT DOCUMENTS

| | | |
|---|---|---|
| WO | 2001068888 A2 | 9/2001 |
| WO | 2002053703 A2 | 7/2002 |
| WO | 2003052051 A2 | 6/2003 |
| WO | 2004111248 A2 | 12/2004 |
| WO | 2005005610 A2 | 1/2005 |
| WO | 2005033321 A2 | 4/2005 |
| WO | 2008124724 A1 | 10/2008 |
| WO | 2013170078 A1 | 11/2013 |
| WO | 2013173512 A2 | 11/2013 |
| WO | 2015/121501 | 2/2015 |
| WO | 2017147477 A1 | 2/2017 |
| WO | 2017106236 A1 | 6/2017 |
| WO | 2019006046 A2 | 1/2019 |

OTHER PUBLICATIONS

Aslanidi et al. "Optimization of the capsid of recombinant adeno-associated virus 2 (AAV2) vectors: the final threshold?." PloS one 8.3 (2013): e59142.

De Silva et al. "Single residue AAV capsid mutation improves transduction of photoreceptors in the Abca4-/- mouse and bipolar cells in the rd1 mouse and human retina ex vivo." Gene Therapy 23(11): 767-774 (2016).

Perabo et al. "In vitro selection of viral vectors with modified tropism: the adeno-associated virus display." Molecular therapy 8.1 (2003): 151-157.

Wooley et al. "A directed evolution approach to select for novel Adeno-associated virus capsids on an HIV-1 producer T cell line." Journal of virological methods 250 (2017): 47-54.

Wu et al. "Mutational analysis of the adeno-associated virus type 2 (AAV2) capsid gene and construction of AAV2 vectors with altered tropism." Journal of Virology 74(18): 8635-8647 (2000).

Tseng et al. "Mapping the AAV capsid host antibody response toward the development of second generation gene delivery vectors." Frontiers in immunology 5: 9 (2014).

UNIPROT. Accession No. A0A513ZUC6_9VIRU. Retrieved from the Internet at <https://www.uniprot.org/uniprotkb/A0A513ZUC6/entry> (2018).

Büning et al. "Capsid modifications for targeting and improving the efficacy of AAV vectors." Molecular Therapy—Methods & Clinical Development 12: 248-265 (2019).

(Continued)

*Primary Examiner* — Fereydoun G Sajjadi  
*Assistant Examiner* — Joel D Levin  
(74) *Attorney, Agent, or Firm* — NIXON PEABODY LLP; David S. Resnick; Mark J. Fitzgerald

(57) ABSTRACT

The technology described herein provides variant adeno-associated viral capsid polypeptides and viruses comprising the same. Such variant viral capsid polypeptides bear a mutation relative to SEQ ID NO: 2 (WT AAV2) in a region corresponding to amino acids 561-588, wherein the region corresponding to amino acids 561-588 comprises a sequence selected from SEQ ID NO: 4-41,337. Further provided herein are methods for delivering a viral payload using viruses comprising variant capsid polypeptides described herein.

18 Claims, 1 Drawing Sheet

Specification includes a Sequence Listing.

(56)                    References Cited

OTHER PUBLICATIONS

Kanaan et al. "Rationally engineered AAV capsids improve transduc-
tion and volumetric spread in the CNS." Molecular Therapy—
Nucleic Acids 8: 184-197 (2017).
Yu et al. "A muscle-targeting peptide displayed on AAV2 improves
muscle tropism on systemic delivery." Gene therapy 16.8: 953-962
(2009).
Gao et al. "Clades of Adeno-associated viruses are widely dissemi-
nated in human tissues." Journal of virology 78.12: 6381-6388
(2004).
Gao. "Adeno-associated virus isolate hu. 63 capsid protein VP1 (cap
gene, complete cds." Retrieved from NCBI Database, accession No.
AY530624 (2004).

* cited by examiner

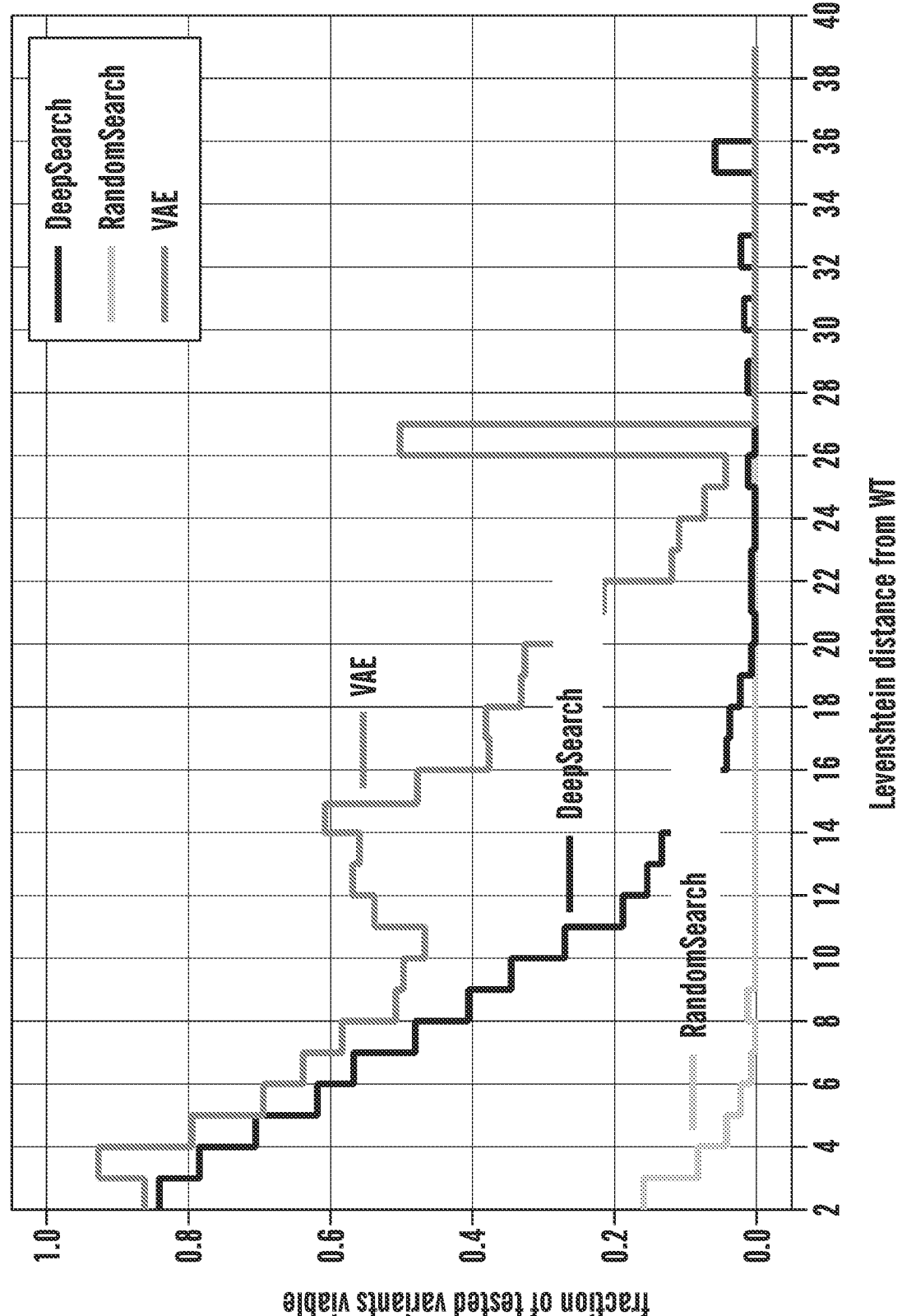

ENGINEERED VIRAL CAPSID POLYPEPTIDES AND USES THEREOF

CROSS-REFERENCE TO RELATED APPLICATIONS

This application is a 35 U.S.C. § 371 National Phase Entry Application of International Application No. PCT/US2020/059294 filed Nov. 6, 2020, which designates the U.S. and claims benefit under 35 U.S.C. § 119 (e) of U.S. Provisional Application No. 62/932,646 filed Nov. 8, 2019, the content of which is incorporated herein by reference in their entirety.

GOVERNMENT SUPPORT

This invention was made with government support under HG008525 and HG005550 awarded by National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Oct. 30, 2019, is named 002806-096400PL01_SL.txt and is 16,548,992 bytes in size.

TECHNICAL FIELD OF THE INVENTION

This invention is related to engineering viral vectors.

BACKGROUND OF THE INVENTION

Adeno-associated virus (AAV) is an attractive agent for use as gene delivery vector. Its simple structure also makes it an attractive target for genetic improvement programs. Nonetheless, there is a continuing need in the art to improve delivery of DNA using AAV and other viral vectors.

SUMMARY OF THE INVENTION

Described herein are viral vectors comprising a variant sequence of the capsid gene, VP1. Such vectors provide, e.g., an improvement in the degree of tissue targeting, payload packaging, delivery efficiency, etc., attainable with such vectors. In particular, viral vectors with capsid polypeptide mutations that modify tropism of the viral particles relative to particles with wild-type capsid polypeptide are described.

Accordingly, one aspect provided herein is a viral capsid polypeptide bearing a mutation relative to SEQ ID NO: 2 (WT AAV2) in a region corresponding to amino acids 561-588.

In one embodiment of any aspect provided herein, the region corresponding to amino acids 561-588 comprises a sequence selected from SEQ ID NO: 4-41,337.

In one embodiment of any aspect provided herein, the capsid is an AAV capsid. In one embodiment of any aspect provided herein, the capsid is an AAV2 capsid.

In one embodiment of any aspect provided herein, the only variation relative to a wild-type AAV viral capsid is in the region corresponding to amino acids 561-588 of SEQ ID NO: 2.

Another aspect described herein provides an AAV VP1 capsid polypeptide bearing a mutation in the region corresponding to amino acids 561-588 of SEQ ID NO: 2.

In one embodiment of any aspect provided herein, the region corresponding to amino acids 561-588 of SEQ ID NO: 2 comprises a sequence selected from SEQ ID NO: 4-41,337.

In one embodiment of any aspect provided herein, the AAV VP1 polypeptide described herein is an AAV2 capsid polypeptide.

Another aspect described herein provides a viral capsid polypeptide comprising a sequence of SEQ ID NO: 2, wherein the region of amino acids 561-588 of SEQ ID NO: 2 comprises a variant sequence selected from SEQ ID NO: 4-41,337.

Another aspect described herein provides a variant of the viral capsid polypeptide of SEQ ID NO: 2, wherein the region of amino acids 561-588 comprises a sequence selected from SEQ ID NO: 4-41,337.

Another aspect described herein provides an AAV2 capsid polypeptide comprising a sequence of SEQ ID NO: 2, wherein the region of amino acids 561-588 of SEQ ID NO: 2 comprises a variant sequence selected from SEQ ID NO: 4-41,337.

Another aspect described herein provides an engineered AAV vector having at least one viral capsid polypeptide comprising any of the capsid polypeptides described herein.

Another aspect described herein provides a nucleic acid encoding any of the capsid polypeptide described herein.

Another aspect described herein provides a viral particle comprising any of the capsid polypeptide described herein.

Another aspect described herein provides a method for delivering a payload, the method comprising contacting a cell with any of the engineered AAV vectors described herein, or any of the viral particles described herein.

In one embodiment of any aspect provided herein, the contacting is sufficient to allow for expression of the payload in the cell.

Another aspect described herein provides a method for administering a payload, the method comprising administering to a subject any of the engineered AAV vectors described herein, or any of the viral particles described herein.

In one embodiment of any aspect provided herein, the administering is sufficient to allow for expression of the payload in the cell.

In one embodiment of any aspect provided herein, the payload is selected from the group consisting of: a nucleic acid, a polypeptide, an inhibitory RNA, an antibody or antibody reagent, an oligonucleotide, and an miRNA.

In yet another aspect, provided herein is a cell comprising a variant capsid polypeptide described herein or a polynucleotide encoding same. For example, a cell comprising a viral particle, where the viral particle comprises a variant capsid polypeptide described herein.

In still another aspect provided herein is a composition, e.g., a pharmaceutical composition comprising a variant capsid polypeptide described herein or a polynucleotide encoding same.

BRIEF DESCRIPTION OF THE DRAWINGS

FIG. 1 is a plot showing the proportion of attempted variants that demonstrate viable packaging ability using each method (VAE and DeepSearch). We include as baseline the success of random sampling for comparison.

DETAILED DESCRIPTION OF THE INVENTION

Described herein are viral vectors containing amino acid mutations in the capsid protein, VP1. Such vectors provide improvements in various functions of the viral vector, e.g., improvement in the degree of tissue targeting (e.g., tropism), payload packaging, delivery efficiency, etc. relative to vectors with wild-type capsid polypeptide. Alternatively, a viral vector comprising a mutated VP1 sequence has a decreased function, e.g., reduced or broadened tropism, relative to vectors with wild-type capsid polypeptide. In one embodiment, a viral vector comprising a mutated VP1 polypeptide comprises an improvement or reduction in at least two functions of the viral vector.

Mutations can be combined together in a single viral nucleic acid or a single viral protein sequence for improved properties. The following describes mutations to viral capsid polypeptides that permit viral genome packaging, yet modify viral vector function, including but not limited to, tropism, either positively, negatively, or both when mutations are combined, relative to given tissues or cell types. Also described are methods of using mutated viral capsid polypeptides and viral vectors comprising them to introduce nucleic acids to desired tissue or cell types, e.g., with improved selectivity for those tissue or cell types. The following provides description of various mutations and considerations for their use to generate viral vectors with improved properties. Mutant capsid proteins and nucleic acids encoding them can be used, e.g., for further viral improvement, for virus preparation and manufacture, and for safety and efficacy studies.

Mutant Capsid Polypeptides

One aspect of the technology described herein provides a viral capsid polypeptide bearing a mutation relative to SEQ ID NO: 2 in a region that corresponds to amino acids 561-588 (SEQ ID NO: 3). SEQ ID NO: 2 is an amino acid sequence encoding wild-type AAV2 capsid protein.

(SEQ ID NO: 2)
MAADGYLPDWLEDTLSEGIRQWWKLKPGPPPPKPAERHKDDSRGLV

LPGYKYLGPFNGLDKGEPVNEADAAALEHDKAYDRQLDSGDNPYLK

YNHADAEFQERLKEDTSFGGNLGRAVFQAKKRVLEPLGLVEEPVKTA

PGKKRPVEHSPVEPDSSSGTGKAGQQPARKRLNFGQTGDADSVPDPQ

PLGQPPAAPSGLGTNTMATGSGAPMADNNEGADGVGNSSGNWHCDS

TWMGDRVITTSTRTWALPTYNNHLYKQISSQSGASNDNHYFGYSTPW

GYFDFNRFHCHFSPRDWQRLINNNWGFRPKRLNFKLFNIQVKEVTQN

DGTTTIANNLTSTVQVFTDSEYQLPYVLGSAHQGCLPPFPADVFMVPQ

YGYLTLNNGSQAVGRSSFYCLEYFPSQMLRTGNNFTFSYTFEDVPFHS

SYAHSQSLDRLMNPLIDQYLYYLSRTNTPSGTTTQSRLQFSQAGASDIR

DQSRNWLPGPCYRQQRVSKTSADNNNSEYSWTGATKYHLNGRDSLV

NPGPAMASHKDDEEKFFPQSGVLIFGKQGSEKTNVDIEKVMITDEEEIR

TTNPVATEQYGSVSTNLQRGNRQAATADVNTQGVLPGMVWQDRDV

YLQGPIWAKIPHTDGHFHPSPLMGGFGLKHPPPQILIKNTPVPANPSTTF

-continued
SAAKFASFITQYSTGQVSVEIEWELQKENSKRWNPEIQYTSNYNKSVN

VDFTVDTNGVYSEPRPIGTRYLTRNL

SEQ ID NO: 3 is an amino acid sequence encoding the amino acid region between amino acids 561-588 of SEQ ID NO: 2.

(SEQ ID NO: 3)
DEEEIRTTNPVATEQYGSVSTNLQRGNR

In one embodiment, the region corresponding to amino acids 561-588 comprises a sequence selected from SEQ ID NO:4-41,337.

In one embodiment, the capsid is an AAV capsid. In one embodiment, the capsid is an AAV2 capsid.

Further provided herein is an AAV VP1 capsid polypeptide bearing a mutation in the region corresponding to amino acids 561-588 of SEQ ID NO: 2. In one embodiment, the region corresponding to amino acids 561-588 of SEQ ID NO: 2 comprises a sequence selected from SEQ ID NO: 4-41,337. In one embodiment of any aspect provided herein, the AAV VP1 polypeptide described herein is an AAV2 capsid polypeptide.

Further provided herein is a viral capsid polypeptide comprising a sequence of SEQ ID NO: 2, wherein the region of amino acids 561-588 comprises a sequence SEQ ID NO: 4-41,337.

Further provided herein is a variant of the viral capsid polypeptide of SEQ ID NO: 2, wherein the region of amino acids 561-588 comprises a sequence of SEQ ID NO: 4-41, 337.

Viruses are typically tropic for certain types of cells and or tissues in the natural host. In one embodiment, a mutant (i.e., variant) sequence of VP1 described herein alters tropism of the virus comprising the variant sequence. As used herein the term "alters tropism" refers to a mutation or set of mutations that changes the efficiency with which a viral vector delivers a nucleic acid to a given tissue or cell type, e.g., blood, brain, heart, kidney, liver, lung, or spleen, among others. In other words, a viral vector comprising a variant viral capsid polypeptide described herein exhibits altered characteristics in comparison to a viral vector comprising the wild-type capsid polypeptide, e.g., a polypeptide of SEQ ID NO: 2, including but not limited to, altered cellular or tissue tropism, cellular or tissue transduction, and/or antigenic properties.

The tropism of a virus or viral vector is generally defined by the structure of its outer surface that interacts with receptors or other cell surface determinants on target cells. For AAV vectors, among others, viral vector tropism is determined primarily by viral capsid polypeptides, and as described herein, the tropism of such vectors can be changed by changing the amino acid sequence of the viral capsid polypeptide. An amino acid change that changes the efficiency of viral vector delivery of a nucleic acid to a target cell or tissue type by at least 10% relative to a reference vector, often, but not necessarily relative to a wild-type vector, is an altered tropism. To be clear, an altered tropism can be an increase/enrichment by at least 10% (1.1×) or a decrease/de-enrichment by at least 10% (0.9×).

The term "tropism" refers to the ability of a viral vector to infect one or more specified cell types, but can also encompass how the vector functions to transduce the cell in the one or more specified cell types. In other words, tropism refers to preferential entry of the viral vector into certain cell or tissue type(s) and/or preferential interaction with the cell surface that facilitates entry into certain cell or tissue types, optionally and preferably followed by expression (e.g., transcription and, optionally, translation) of a transgene carried by the viral vector/particle in the cell. As used herein, the term "tropism profile" refers to the pattern of transduction of one or more target cells, tissues and/or organs.

As used herein, the term "transduction" refers to the introduction, by a viral vector, of a genetic payload and expression of one or more genes encoded therein. Thus, transduction refers to entry of the vector into the cell and the transfer of genetic material contained within the vector into the cell to obtain expression from the vector genome. In some cases, but not all cases, transduction and tropism may correlate.

As used here, "systemic tropism" and "systemic transduction" (and equivalent terms) indicate that the viral vector exhibits tropism for or transduces, respectively, tissues throughout the body (e.g., brain, lung, skeletal muscle, heart, liver, kidney and/or pancreas).

Methods for measuring viral vector tropism are known in the art. For example, viral vector tropism can be determined by measuring the ability of viral vector to transduce transgene in a cell of interest. This can be measured by the expression of a reporter protein and compared to a control viral vector, e.g., wild-type viral vector. Some exemplary reporter proteins include, but are not limited to, GFP, YFP, red cherry, β-galactosidase, or other reporter proteins known in the art.

In one embodiment, the mutation of the capsid polypeptide increases tropism, e.g., the virus comprising the mutated viral capsid polypeptide more efficiently delivers nucleic acid to the target cell type as compared a virus comprising a wild-type, or other reference, viral capsid polypeptide. In one embodiment, tropism is at least 1.1-fold (e.g., 10% greater than reference level, or 110% of the level reference level) more efficient as compared to a wild-type, or other reference, viral capsid polypeptide. In one embodiment, the delivery of a nucleic acid is at least 1.5-fold, at least 2-fold, at least 4-fold, at least 5-fold, at least 10-fold, or more, more efficient as compared to a virus comprising the wild-type viral capsid polypeptide. One of ordinary skill in the art can measure the delivery efficiency of a viral particle comprising any of the viral capsid polypeptides described herein, e.g., using PCR-based assays on an isolated targeted cell or tissue type (e.g., blood, heart, kidney, liver, lung, or spleen) to assess if the nucleic acid is delivered to and/or expressed in that targeted cell type. The expression of the nucleic acid delivered by a viral particle comprising either a viral capsid polypeptide as described herein or a wild-type, or other reference, viral capsid polyprotein can be compared to determine the change in expression as a measure of the efficiency of delivery.

In some embodiments of any one of the aspects, a viral vector comprising a variant viral capsid polypeptide as described herein exhibits increased tropism, as compared to a wild-type, or other reference, viral capsid polypeptide, for a cell or tissue selected from skeletal muscle, cardiac muscle, diaphragm muscle, pancreas (including (β-islet spleen, the gastrointestinal tract (e.g., epithelium and/or smooth muscle), cells of the central nervous system, liver, lung, joint cells, and/or kidney. For example, a viral vector comprising a variant viral capsid polypeptide as described herein exhibits increased tropism for a tissue or cell type selected from blood, brain, heart, kidney, liver, lung, and spleen.

In one embodiment, the mutation of the capsid polypeptide decreases tropism, e.g., the virus comprising the mutated viral capsid polypeptide delivers nucleic acid to a broader range of target cell types as compared to a virus comprising the wild-type, or other reference, viral capsid polypeptide. In one embodiment, the tropism is decreased by at least 10%. In other embodiments, the tropism is decreased by at least 20%, at least 30%, at least 40%, at least 50%, at least 60%, at least 70%, at least 80%, at least 90%, at least 99%, or more as compared to a virus comprising the wild-type, or other reference, viral capsid polypeptide. One skilled in the art can assess tropism of a virus using standard techniques, e.g., measuring local expression of a virus following in vivo delivery.

In some embodiments of any one of the aspects, a viral vector comprising a variant viral capsid polypeptides described herein exhibits a decreased tropism, as compared to a wild-type, or other reference, viral capsid polypeptide, for a cell or tissue selected from skeletal muscle, cardiac muscle, diaphragm muscle, pancreas (including (β-islet cells), spleen, the gastrointestinal tract (e.g., epithelium and/or smooth muscle), cells of the central nervous system, liver, lung, joint cells, and/or kidney. For example, a viral vector comprising a variant viral capsid polypeptides described herein exhibits decreased tropism for a tissue or cell type selected from blood, brain, heart, kidney, liver, lung, and spleen.

Variant VP1 polypeptides have been identified and assessed for effects on viral DNA packaging and viral infectivity of particular tissues. In one embodiment, the viral packaging is increased by at least 10%. In other embodiments, the viral packaging is increased or altered by at least 20%, at least 30%, at least 40%, at least 50%, at least 60%, at least 70%, at least 80%, at least 90%, at least 99%, or more as compared to a virus comprising the wild-type, or other reference, viral capsid polypeptide.

In one embodiment, the viral packaging is decreased by at least 10%. Alterations in packaging include, but are not limited to alterations in the rate or efficiency of packaging, or, for example, alterations in the amount of vector sequence that can be packaged while retaining viral infectivity. In one embodiment, the viral infectivity is increased by at least 10% or more. In one embodiment, the viral infectivity is increased by 10%. In other embodiments, the viral infectivity is increased by 20%, 30%, 40%, 50%, or more as compared to a virus comprising the wild-type viral capsid polypeptide. In one embodiment, the viral infectivity is decreased by at least 10%. In other embodiments, the viral infectivity is decreased by at least 20%, at least 30%, at least 40%, at least 50%, at least 60%, at least 70%, at least 80%, at least 90%, at least 99%, or more as compared to a virus comprising the wild-type, or other reference, viral capsid polypeptide. A decreased in infectivity can be tolerated, e.g., where there are other beneficial changes provided by the mutation. Viral packaging and infectivity can be assessed by one skilled in the art using standard techniques, e.g., measuring the viral titer in a sample that has been contacted with an AAV virus or viral particle comprising any of the viral capsid polypeptides described herein.

Particular regions of AAV2 capsid protein tolerate amino acid alterations, e.g., deletion, insertion, or substitution better than others, and changes to certain regions that tolerate such change can have pronounced impact on viral vector tropism, among other functions. The region of the AAV2 capsid polypeptide of SEQ ID NO: 3, which is amino acids 561-588 of SEQ ID NO: 2, is identified herein as being tolerant of a variety of changes.

One aspect of the technology described herein is a nucleic acid, e.g., a polynucleotide encoding any of the viral capsid polypeptides described herein. One skilled in the art can alter the wild-type VP1 sequence (SEQ ID NO: 1), e.g., by introducing at least one base pair substitution, such that the altered sequence encodes a variant amino acid sequence. The nucleic acid sequence for each codon is known in the art and presented herein in Table 1. For example, to alter an amino acid from an isoleucine (which is translated by the nucleotide sequence AUU) to valine (which is translated by the nucleotide sequence GUU), one would change the first nucleotide from an A to G. In one embodiment, the nucleic acid sequence of SEQ ID NO: 1 is altered such that the region of amino acids 561-588 of the altered sequence encodes a sequence of SEQ ID NO: 4-41,337. Site-directed mutagenesis is known in the art and can be used to introduce a point mutation(s) (e.g., amino acid substitutions, insertions, or deletions) or other mutations or combinations thereof to a viral capsid polypeptide. Site-directed mutagenesis is further described in, e.g., Li B, et al. *Hum Gene Ther Methods.* 2015 December: 26(6):211-20, and Bachman, *J. Methods Enzymol.* 2013; 529:241-248, which are incorporated herein by reference in their entireties.

In one embodiment, the nucleotide sequence comprises at least 1 point mutation. In one embodiment, the nucleotide sequence comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84 or more point mutations.

In some embodiments, the nucleotide sequence comprises no more than 2, no more than 3, no more than 4, no more than 5, no more than 6, no more than 7, no more than 8, no more than 9, no more than 10, no more than 11, no more than 12, no more than 13, no more than 14, no more than 15, no more than 16, no more than 17, no more than 18, no more than 19, no more than 20, no more than 21, no more than 22, no more than 23, no more than 24, no more than 25, no more than 26, no more than 27, no more than 28, no more than 29, no more than 30, no more than 31, no more than 32, no more than 33, no more than 34, no more than 35, no more than 36, no more than 37, no more than 38, no more than 39, no more than 40, no more than 41, no more than 42, no more than 43, no more than 44, no more than 45, no more than 46, no more than 47, no more than 48, no more than 49, no more than 50, no more than 51, no more than 52, no more than 53, no more than 54, no more than 55, no more than 56, no more than 57, no more than 58, no more than 59, no more than 60, no more than 61, no more than 62, no more than 63, no more than 64, no more than 65, no more than 66, no more than 67, no more than 68, no more than 69, no more than 70, no more than 71, no more than 72, no more than 73, no more than 74, no more than 75, no more than 76, no more than 77, no more than 78, no more than 79, no more than 80, no more than 81, no more than 82, no more than 83, or no more than 84 point mutations.

In one embodiment, the nucleotide sequence comprises at least 1 point mutation in the region encoding amino acids 561-588 of SEQ ID NO: 2. For example, the nucleotide sequence comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, or 84 point mutations in the region encoding amino acids 561-588 of SEQ ID NO: 2.

In some embodiments, the nucleotide sequence comprises no more than 1, no more than 2, no more than 3, no more than 4, no more than 5, no more than 6, no more than 7, no more than 8, no more than 9, no more than 10, no more than 11, no more than 12, no more than 13, no more than 14, no more than 15, no more than 16, no more than 17, no more than 18, no more than 19, no more than 20, no more than 21, no more than 22, no more than 23, no more than 24, no more than 25, no more than 26, no more than 27, no more than 28, no more than 29, no more than 30, no more than 31, no more than 32, no more than 33, no more than 34, no more than 35, no more than 36, no more than 37, no more than 38, no more than 39, no more than 40, no more than 41, no more than 42, no more than 43, no more than 44, no more than 45, no more than 46, no more than 47, no more than 48, no more than 49, no more than 50, no more than 51, no more than 52, no more than 53, no more than 54, no more than 55, no more than 56, no more than 57, no more than 58, no more than 59, no more than 60, no more than 61, no more than 62, no more than 63, no more than 64, no more than 65, no more than 66, no more than 67, no more than 68, no more than 69, no more than 70, no more than 71, no more than 72, no more than 73, no more than 74, no more than 75, no more than 76, no more than 77, no more than 78, no more than 79, no more than 80, no more than 81, no more than 82, no more than 83, or no more than 84 point mutations in the region encoding amino acids 561-588 of SEQ ID NO: 2.

In one embodiment, the nucleic acid sequence is altered such that it encodes at least 1 variant amino acid. In one embodiment, the nucleic acid sequence is altered such that it encodes at least 2, 3, 4, 5, 6, 7, 8, 9, 10, 11, 12, 13, 14, 15, 16, 17, 18, 19, 20, 21, 22, 23, 24, 25, 26, 27, 28 or more variant amino acids. For clarity, it is noted that a variant amino acid means an amino acid that is different from the one encoded by a nucleic acid sequence encoding SEQ ID NO: 2.

In some embodiments, the nucleic acid sequence is altered such that it encodes no more than 2, no more than 3, no more than 4, no more than 5, no more than 6, no more than 7, no more than 8, no more than 9, no more than 10, no more than 11, no more than 12, no more than 13, no more than 14, no more than 15, no more than 16, no more than 17, no more than 18, no more than 19, no more than 20, no more than 21, no more than 22, no more than 23, no more than 24, no more than 25, no more than 26, no more than 27, or no more than 28 variant amino acids.

In one embodiment, the nucleic acid sequence is altered such that it encodes at least 1 variant amino acid in the region corresponding to amino acids 561-588 of SEQ ID NO: 2. For Example, the nucleic acid sequence is altered such that it encodes at least 2, 3, 4, 5, 6, 7, 8, 9, 10, 11, 12, 13, 14, 15, 16, 17, 18, 19, 20, 21, 22, 23, 24, 25, 26, 27, 28 or more variant amino acids in the region corresponding to amino acids 561-588 of SEQ ID NO: 2.

In some embodiments, the nucleic acid sequence is altered such that it encodes no more than 2, no more than 3, no more than 4, no more than 5, no more than 6, no more than 7, no more than 8, no more than 9, no more than 10, no more than 11, no more than 12, no more than 13, no more than 14, no more than 15, no more than 16, no more than 17, no more than 18, no more than 19, no more than 20, no more than 21, no more than 22, no more than 23, no more than 24, no more than 25, no more than 26, no more than 27, or no more than 28 variant amino acids in the region corresponding to amino acids 561-588 of SEQ ID NO: 2.

TABLE 1

Nucleotide codons for amino acids

| AA | Codons |
|---|---|
| Ala | GCT, GCC, GCA, GCG |
| Arg | CGT, CGC, CGA, CGG, AGA, AGG |
| Asn | AAT, AAC |
| Asp | GAT, GAC |
| Cys | TGT, TGC |
| Gln | CAA, CAG |
| Glu | GAA, GAG |
| Gly | GGT, GGC, GGA, GGG |
| His | CAT, CAC |
| Ile | ATT, TAC, ATA |
| Leu | TTA, TTG, CTT, CTA, CTG |
| Lys | AAA, AAG |
| Met | ATG |
| Phe | TTT, TTC |
| Pro | CCT, CCC, CCA, CCG |
| Ser | TCT, TCC, TCA, TCG, AGT, AGC |
| Thr | ACT, ACC, ACA, ACG |
| Trp | TGG |
| Tyr | TAT, TAC |
| Val | GTT, GTC, GTA, GTG |
| Start | ATG |
| Stop | TAA, TGA, TAG |

In some embodiments, a polynucleotide encoding a variant viral capsid polypeptide described herein is operably linked to a promoter sequence, for example, a promoter sequence that drives expression of the polynucleotide in a cell. In some embodiments, the polynucleotide further comprises a sequence that encodes a REP protein, e.g., an AAV rep protein. In some embodiments, the polynucleotide further comprises a sequence that encodes a CAP protein, e.g., an AAV CAP protein.

Another aspect of the technology described herein is a viral particle comprising any of the viral capsid polypeptides described herein. It is noted that a viral particle comprising a variant capsid polypeptide as described herein can be replication-competent or replication-incompetent. Thus, in some embodiments, the viral particle comprising a variant capsid polypeptide as described herein is replication-competent. As used herein, the term "replication-competent" refers to a virus or viral particle that is infectious, and is also capable of being replicated in an infected cell (i.e. in the presence of a helper virus or helper virus functions). In the case of AAV, replication competence generally requires the presence of functional AAV packaging genes.

In some other embodiments, the viral particle comprising a variant capsid polypeptide as described herein is replication-incompetent or replication defective. As used herein, the terms "replication-incompetent" and "replication defective" refer to a virus or viral particle that cannot independently replicate and package its genome. For example, when a cell is infected with the virus or viral particle, the heterologous gene is expressed in the infected cells, however, the virus or the viral particle is not able to replicate further.

In some embodiments, the viral particle further comprises a polynucleotide encoding a transgene, e.g., a polynucleotide comprising a sequence that encodes a gene product such as a therapeutic gene product. In some embodiments, the polynucleotide is flanked on the 5' and 3' ends by functional AAV inverted terminal repeat (ITR) sequences. By "functional AAV ITR sequences" is meant that the ITR sequences function as intended for the rescue; replication and packaging of the AAV virion. Hence; AAV ITRs for use in the gene delivery vectors need not have a wild-type nucleotide sequence, and can be altered by the insertion, deletion or substitution of nucleotides or the AAV ITRs can be derived from any of several AAV serotypes, e.g. AAV1, AAV2, AAV3, AAV4, AAV5, AAV6, AAV7, AAV8, AAV9, and AAV10. In some embodiments, the viral particles have the wild type REP and CAP genes deleted in whole or part, but retain functional flanking ITR sequences.

One skilled in the art can make viral particles comprising a variant capsid polypeptide described herein using standard methods. For example, an AAV expression vector comprising a polynucleotide cassette can be introduced into a producer cell, followed by introduction of an AAV helper construct comprising a polynucleotide sequence encoding a variant capsid polypeptide described herein, and where the helper construct includes AAV coding regions capable of being expressed in the producer cell and which complement AAV helper functions absent in the AAV vector. This is followed by introduction of helper virus and/or additional vectors into the producer cell, wherein the helper virus and/or additional vectors provide accessory functions capable of supporting efficient rAAV virus production. The producer cells are then cultured to produce rAAV. Some exemplary methods for producing viral particles amenable to the presently disclosed technology are described, for example, in U.S. Pat. Nos. 5,436,146; 5,753,500; 6,040,183, 6,093,570 and 6,548,286, contents of each of which is incorporated herein by reference in their entireties.

In one example, viral particles comprising a variant polypeptide described herein can be produced by first generating a DNA library of AAV capsid variants. Libraries of AAV2 capsid gene sequence variants are cloned into a plasmid containing the AAV Inverted Terminal Repeat regions (ITRs). The final ITR plasmids contain, e.g., a cytomegalovirus (CMV) promoter upstream of the Cap gene. AAV virus libraries are produced from the DNA libraries. The capsid library plasmids, AAV pHelper plasmids, and plasmids containing the AAV2 Rep gene are co-transfected into HEK-293T cells using PEI. Capsids are purified using standard techniques for cell lysis (freeze-thaw or addition of 5 M NaCl), treatment with benzonase to remove unpackaged genomes, and purification and concentration by iodixanol ultra-centrifugation.

In preparing the viral particles, any host cells for producing recombinant viral particles can be employed, including, for example, mammalian cells, insect cells, plant cells, microorganisms and yeast. Host cells can also be packaging cells in which the AAV rep and cap genes are stably maintained in the host cell or producer cells in which the AAV vector genome is stably maintained and packaged. Exemplary packaging and producer cells include but are not limited to HeLa cells, COS cells, COS-1 cells, COS-7 cells, HEK293 cells, A549 cells, BHK cells, BSC-1 cells, BSC-40 cells, Vero cells, Sfc9 cells, Sf-21 cells, Tn-368 cells, BTI-Tn-5B1-4 (High-Five) cells, Saos cells, C2C12 cells, L cells, HT1080 cells, HepG2 cells, WEHI cells, 3T3 cells, 10T1/2 cells, MDCK cells, BMT-10 cells, WI38 cells, or primary fibroblast, hepatocyte or myoblast cells derived from mammals.

In vivo packaging ability of viral capsid variants was measured, e.g., using methods described herein above. The number of viruses that were packaged ("virus") compared to the number of input viral genomes ("plasmid") were determined. Measuring the frequency of capsid (or other library component) mutants before and after selection reveals which mutations are beneficial and which are deleterious based on the particular selection method.

Also provided herein is a cell comprising a variant viral capsid polypeptide described herein or a polynucleotide encoding a variant viral capsid polypeptide described herein. The cell can be a prokaryotic cell or a eukaryotic cell. For example, the cell can be a mammalian cell, insect cell, plant cell, bacterial cell or yeast cell. Some exemplary cells include, but are not limited to, alveolar cells, basophils, cardiac smooth muscle cells, cardiomyocytes, collecting duct intercalated cells, collecting duct principal cells, ectodermal cells, endocardial cells, endoderm cells, eosinophils, epithelial cells, hepatic stellate cells, interstitial kidney cells, intrahepatic lymphocytes, kidney distal tubule cells, kidney glomerulus parietal cells, kidney glomerulus podocytes, kidney proximal tubule brush border cells, loop of Henle thin segment cells, lung epithelial cells, lung smooth muscle cells, lymphocytes, monocytes, muscle cells, neutrophils, non-parenchymal cells, parenchymal cells, phagocytic Kupffer cells, platelets, red blood cells, sinusoidal endothelial cells, splenic endothelial cells, splenic fibroblasts, splenocytes, and thick ascending limb cells.

In some embodiments, the cell can be a cell used for producing a viral particle, e.g., a producer cell.

In some embodiments, the cell can be a cell which has been transduced, infected, transfected or transformed with a viral vector described herein. Typically, a cell is referred to as "transduced", "infected"; "transfected" or "transformed" dependent on the means used for administration, introduction or insertion of heterologous DNA (i.e., the viral vector) into the cell.

Also provided herein are pharmaceutical compositions comprising a variant capsid polypeptide described herein or a polynucleotide encoding same and one or more pharmaceutically acceptable diluent, carrier, or excipient. For example, the composition can comprise a viral particle comprising a variant capsid polypeptide described herein. In some embodiments, the composition can comprise a cell, wherein the cell comprises a variant capsid polypeptide described herein or a polynucleotide encoding same.

For example, the variant capsid polypeptide or a polynucleotide encoding same (as is or as encompassed in a viral particle or cell) can be combined with pharmaceutically-acceptable carriers, diluents and reagents useful in preparing a formulation that is generally safe, non-toxic, and desirable, and includes excipients that are acceptable for primate use. Such excipients can be solid, liquid, semisolid, or, in the case of an aerosol composition, gaseous. Examples of such carriers or diluents include, but are not limited to, water, saline, Ringer's solutions, dextrose solution, and 5% human serum albumin. Supplementary active compounds can also be incorporated into the formulations. Solutions or suspensions used for the formulations can include a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates; detergents such as Tween 20 to prevent aggregation; and compounds for the adjustment of tonicity such as sodium chloride or dextrose. The pH can be adjusted with acids or bases, such as hydrochloric acid or sodium hydroxide. In particular embodiments, the pharmaceutical compositions are sterile. For instances in which ocular cells are to be contacted in vivo, the subject polynucleotide cassettes or gene delivery vectors comprising the subject polynucleotide cassette can be treated as appropriate for delivery to the eye.

Pharmaceutical compositions can further include sterile aqueous solutions or dispersions and sterile powders for the extemporaneous preparation of sterile injectable solutions or dispersion. For intravenous administration, suitable carriers include physiological saline, bacteriostatic water, or phosphate buffered saline (PBS). In some cases, the composition is sterile and should be fluid to the extent that easy syringability exists. In certain embodiments, it is stable under the conditions of manufacture and storage and is preserved against the contaminating action of microorganisms such as bacteria and fungi. The carrier can be, e.g., a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the internal compositions can be brought about by including in the composition an agent which delays absorption, for example, aluminum monostearate and gelatin.

Corresponding Mutations

Mutations at corresponding locations in, for example homologous viral capsid polypeptides, would be expected to have similar effects on viral function. Corresponding locations can include, for example, a location relative to the full length capsid polypeptide (e.g., SEQ ID NO: 2), or for that matter, a location relative to a sub-domain or sub-region of the full length capsid polypeptide (e.g., SEQ ID NO: 3). In one aspect, a viral capsid polypeptide is provided herein that bears a mutation that corresponds to a mutation of the polypeptide of SEQ ID NO: 2, e.g., SEQ ID NO: 4-41,337, as described herein. In one embodiment, a homologous viral capsid polypeptide has at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more sequence identity to wild-type AAV2 capsid protein (e.g., SEQ ID NO: 2). In another embodiment, the viral capsid polypeptides of AAV serotypes 1, and 3-13 are homologous to an AAV2 capsid polypeptide.

One aspect described herein is a viral capsid polypeptide comprising a region corresponding to the amino acid sequence of SEQ ID NO: 3, wherein the region corresponding to the amino acid sequence of SEQ ID NO: 3 comprises a mutation relative to SEQ ID NO: 3 that, e.g., alters the function of the virus comprising the viral capsid polypeptide, wherein the mutation is selected from SEQ ID NO: 4-41,337. In one embodiment, a homologous viral capsid polypeptide has a region with at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more sequence identity to SEQ ID NO: 3.

As noted elsewhere herein, the identification of amino acid sites or regions of amino acid sequence in the AAV2 capsid polypeptide of SEQ ID NO: 2 that tolerate change in general, i.e., that permit functions of the viral vector can be used to guide changes in the capsid polypeptides of other AAV serotypes to similarly influence function or provide for modified properties. Thus, through use of sequence alignment, a mutation or set of mutations that provides a desired change in function for AAV2 capsid polypeptide of SEQ ID NO: 2 can be introduced to the corresponding location of the capsid polypeptide of another AAV serotype to similarly influence those properties in that serotype. It is contemplated that the introduction of changes identified herein in this amino acid 561-588 sub-region of the AAV2 capsid polypeptide to the corresponding region or sub-region of another AAV serotype capsid polypeptide will influence the function of that AAV serotype in a similar manner.

As used herein, "mutation" refers to any change in the amino acid sequence, e.g., a substitution, insertion, or deletion of at least one amino acid. Site-directed mutations in the nucleic acid sequence can be generated by one skilled in the art using techniques known in the art or described herein.

Mutations that are at equivalent positions in other homologous viruses can be made and used for improving, e.g., virus packaging and virus infectivity. Examples of other homologous viruses include any of AAV serotypes 1, and 3-12, as well as other natural isolates or synthetic sequences. Corresponding positions in homologous viruses can be inferred from sequence homology to AAV2. In one embodiment, the mutations described herein are introduced into the corresponding amino acid sequence of an AAV1, AAV3, AAV3B, AAV4, AAV5, AAV6, AAV7, AAV8, AAV9, AAV10, AAV11, AAV12, or AAV13 capsid polypeptide.

Methods for Delivering Nucleic Acid

Provided herein is a method of delivering a payload to a cell comprising contacting a cell with an AAV virus or viral particle comprising any of the viral capsid polypeptides described herein. In one embodiment, the contacting occurs in vitro. In one embodiment, the contacting occurs ex vivo.

The term "contacting" or "contact" as used herein in connection with contacting a cell with an AAV virus or viral particle includes subjecting the cell to an appropriate culture medium which comprises the AAV virus or viral particle. Where the cell is in vivo, "contacting" or "contact" includes administering the AAV virus or viral particle in a pharmaceutical composition to a subject via an appropriate administration route such that the virus or viral particle contacts the cell in vivo.

Further provided herein is a method of delivering a payload in vivo to a target cell, comprising administering an AAV virus or viral particle comprising any of the viral capsid polypeptides described herein to a subject. In one embodiment, in vivo is systemic delivery.

Exemplary target or host cells include blood cells (e.g., red blood cells, platelets, neutrophils, eosinophils, basophils, lymphocytes, or monocytes); heart cells (e.g., cardiomyocyte, endocardial cells, or cardiac smooth muscle cells); muscle cells; epithelial cells; endoderm cells; ectodermal cells; kidney cells (e.g., kidney glomerulus parietal cells, kidney glomerulus podocytes, kidney proximal tubule brush border cells, loop of Henle thin segment cells, thick ascending limb cells, kidney distal tubule cells, collecting duct principal cells, collecting duct intercalated cells, and interstitial kidney cells); liver cells (e.g., parenchymal cells, non-parenchymal cells, sinusoidal endothelial cells, phagocytic Kupffer cells, hepatic stellate cells, and intrahepatic lymphocytes); lung cells (e.g., lung epithelial cells, lung smooth muscle cells, and alveolar cells); and spleen cells (e.g., splenocytes, splenic endothelial cells and splenic fibroblasts).

In vivo delivery of the AAV virus or viral particle can be, for example, by injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, intrasternal injection and infusion. The AAV virus or viral particle can be administered as a single bolus or multiple boluses, as a continuous infusion, or a combination thereof. In some embodiments, the AAV virus or viral particle can be administered into the blood stream of the subject.

The dose of AAV virions or viral particles required to achieve a particular "therapeutic effect," e.g., the units of dose in vector genomes/per kilogram of body weight (vg/kg), will vary based on several factors including, but not limited to: the route of AAV virus or viral particle administration, the level of gene expression required to achieve a therapeutic effect, the specific disease or disorder being treated, a host immune response to the AAV virus or viral particle, a host immune response to the gene expression product, and the stability of the gene product. One of skill in the art can readily determine a AAV virus or viral particle dose range to treat a patient having a particular disease or disorder based on the aforementioned factors, as well as other factors that are well known in the art. Generally speaking, by "therapeutic effect" is meant a level of expression of one or more transgenes in the AAV virus or viral particle sufficient to alter a component of a disease (or disorder) toward a desired outcome or clinical endpoint, such that a patient's disease or disorder shows clinical improvement, often reflected by the amelioration of a clinical sign or symptom relating to the disease or disorder. Exemplary doses for achieving therapeutic effects are AAV virus or viral particle titers of at least about $10^5$, $10^6$, $10^7$, $10^8$, $10^9$, $10^{10}$, $10^{11}$, $10^{12}$, $10^{13}$, $10^{14}$, $10^{15}$, $10^{16}$ transducing units or more. For example, from about $10^8$ to about $10^{13}$ transducing units. It is noted that more than one administration (e.g., two, three, four, or more administrations) can be employed to achieve desired (e.g. therapeutic) levels of gene expression.

Levenshtein Distance

The Levenshtein distance has been calculated for the variant capsid polypeptides described herein. As used herein, the "Levenshtein distance" refers to a string metric for measuring the difference between two sequences. For example, the Levenshtein distance between two sequences is the minimum number of single-base pair edits (i.e. insertions, deletions, or substitutions) required to change one sequence into the other. In one embodiment, the variant capsid polypeptide has a Levenshtein distance of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more as compared to SEQ ID NO: 2 (wild-type VP1). The Levenshtein distance can be calculated by one skilled in the art, e.g., using the formula herein below the Levenshtein distance between two strings a, b (of length |a| and |b| respectively) is given by leva,b(|a|,|b|) where:

$$lev_{a,b}(i, j) = \begin{cases} \max(i, j) & \text{if } \min(i, j) = 0, \\ \min \begin{cases} lev_{a,b}(i-1, j)+1 \\ lev_{a,b}(i, j-1)+1 \\ lev_{a,b}(i-1, j-1)+1_{(a_i \neq b_j)} \end{cases} & \text{otherwise.} \end{cases}$$

where 1(ai≠bi) is the indicator function equal to 0 when ai≠bi and equal to 1 otherwise, and leva, b(i,j) is the distance between the first i characters of a and the first j characters of b.

Note that the first element in the minimum corresponds to deletion (from a to b), the second to insertion and the third to match or mismatch, depending on whether the respective symbols are the same.

Table 2 denotes the SEQ ID NOs that correspond to a particular Levenshtein distance to the wild-type (e.g., SEQ ID NO: 2). The SEQ IN NOs boundaries are inclusive (e.g. start_SEQ ID NO: 10, and end_SEQ ID NO: 15, means both SEQ ID NO: 10 and SEQ ID NO: 15 are included in the range).

TABLE 2

Levenshtein distance of sequences to the wild-type (SEQ ID NO: 2)

| Distance from Wild-type | Start SEQ ID NO | End SEQ ID NO |
|---|---|---|
| 0 | 2 | 3 |
| 2 | 4 | 5946 |
| 3 | 5947 | 14914 |
| 4 | 14915 | 23541 |
| 5 | 23542 | 30508 |
| 6 | 30509 | 36121 |
| 7 | 36122 | 37072 |
| 8 | 37073 | 37874 |
| 9 | 37875 | 38557 |
| 10 | 38558 | 39153 |
| 11 | 39154 | 39632 |
| 12 | 39633 | 39955 |
| 13 | 39956 | 40167 |
| 14 | 40168 | 40326 |
| 15 | 40327 | 40444 |
| 16 | 40445 | 40521 |
| 17 | 40522 | 40597 |
| 18 | 40598 | 40675 |
| 19 | 40676 | 40766 |
| 20 | 40767 | 40880 |
| 21 | 40881 | 41009 |
| 22 | 41010 | 41157 |
| 23 | 41158 | 41251 |
| 24 | 41252 | 41310 |
| 25 | 41311 | 41327 |
| 26 | 41328 | 41331 |
| 28 | 41332 | 41333 |
| 30 | 41334 | 41334 |
| 32 | 41335 | 41335 |
| 35 | 41336 | 41336 |
| 36 | 41337 | 41337 |

Some exemplary embodiments of the invention can be described by the following numbered embodiments:

Embodiment 1: A viral capsid polypeptide bearing a mutation relative to SEQ ID NO: 2 (WT AAV2) in a region corresponding to amino acids 561-588.

Embodiment 2: The viral capsid polypeptide of Embodiment 1, wherein the region corresponding to amino acids 561-588 comprises a sequence selected from SEQ ID NO: 4-41,337.

Embodiment 3: The viral capsid polypeptide of Embodiments 1 or 2, which is an AAV capsid polypeptide.

Embodiment 4: The viral capsid polypeptide of any of Embodiments 1-3, which is an AAV2 capsid polypeptide.

Embodiment 5: An AAV VP1 capsid polypeptide bearing a mutation in the region corresponding to amino acids 561-588 of SEQ ID NO: 2.

Embodiment 6: The AAV VP1 capsid polypeptide of Embodiment 5, wherein the region corresponding to amino acids 561-588 of SEQ ID NO: 2 comprises a sequence selected from SEQ ID NO: 4-41,337.

Embodiment 7: The AAV VP1 capsid polypeptide of Embodiments 5 or 6, which is an AAV2 capsid polypeptide.

Embodiment 8: A viral capsid polypeptide comprising a sequence of SEQ ID NO: 2, wherein the region of amino acids 561-588 of SEQ ID NO: 2 comprises a variant sequence selected from SEQ ID NO: 4-41,337.

Embodiment 9: A variant viral capsid polypeptide of SEQ ID 2, wherein the region of amino acids 561-588 comprises a sequence of SEQ ID NO: 4-41,337.

Embodiment 10: An AAV2 capsid polypeptide comprising a sequence of SEQ ID NO: 2, wherein the region of amino acids 561-588 of SEQ ID NO: 2 comprises a variant sequence selected from SEQ ID NO: 4-41,337.

Embodiment 11: An engineered AAV vector having at least one capsid polypeptide comprising any one of the capsid polypeptides of Embodiments 1-10.

Embodiment 12: A nucleic acid encoding the capsid polypeptide of any one of Embodiments 1-10.

Embodiment 13: A viral particle comprising a capsid polypeptide of any one of Embodiments 1-10.

Embodiment 14: A method for delivering a payload, the method comprising contacting a cell with any of the engineered AAV vectors of Embodiment 12, or viral particles of Embodiment 13.

Embodiment 15: The method of Embodiment 14, wherein the contacting is sufficient to allow for expression of the payload in the cell.

Embodiment 16: A method for administering a payload, the method comprising administering to a subject any of the engineered AAV vectors of Embodiment 12, or viral particles of Embodiment 13.

Embodiment 17: The method of Embodiment 16, wherein the administering is sufficient to allow for expression of the payload in the cell.

Embodiment 18: The method of any of Embodiments 14-17, wherein the payload is selected from the group consisting of: a nucleic acid, a polypeptide, an inhibitory RNA, an antibody or antibody reagent, an oligonucleotide, and a miRNA.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN- 1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties. As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the technology.

The word "or" is intended to include "and" unless the context clearly indicates otherwise.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

The abbreviation, "e.g." is derived from the Latin Exempli gratia, and is used herein to indicate a non-limiting example. Thus, the abbreviation "e.g." is synonymous with the term "for example."

As used herein, the term "viral capsid polypeptide" refers to the proteinaceous shell or coat of a viral particle. At a minimum, a viral capsid polypeptide as described herein permits packaging or assembly of the capsid polypeptide into a viral particle that is competent for delivery of nucleic acid to the host cell. Capsids function to encapsidate, protect, transport, and release into a host cell a viral genome. Capsids are generally comprised of oligomeric structural subunits of a polypeptide of the viral capsid polypeptides. As used herein, the term "encapsidated" means enclosed within a viral capsid. As an example, the AAV genome comprises three overlapping sequences which encode capsid proteins, VP1, VP2 and VP3, which start from one promoter, p40. The AAV capsid is composed of a mixture of VP1, VP2, and VP3 totaling 60 monomers arranged in icosahedral symmetry in a ratio of 1:1:10.

As used herein, "packaging" refers to a series of intracellular events that result in the assembly and encapsidation of an AAV particle.

As used herein, "payload" refers to a nucleic acid which is encapsidated within a viral vector, e.g., an AAV vector. A payload nucleic acid can encode, e.g., a polypeptide, an inhibitory RNA, an antibody or antibody reagent, an oligonucleotide, or a miRNA.

The term "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a nonpolypeptide moiety covalently or noncovalently associated therewith is still considered a "polypeptide." Exemplary modifications include glycosylation and palmitoylation. Polypeptides can be purified from natural sources, produced using recombinant DNA technology or synthesized through chemical means such as conventional solid phase peptide synthesis, etc. The term "polypeptide sequence" or "amino acid sequence" as used herein can refer to the polypeptide material itself and/or to the sequence information (i.e., the succession of letters or three letter codes used as abbreviations for amino acid names) that biochemically characterizes a polypeptide. A polypeptide sequence presented herein is presented in an N-terminal to C-terminal direction unless otherwise indicated.

A given amino acid can be replaced by a residue having similar physicochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. ligand-mediated receptor activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, a polypeptide described herein (or a nucleic acid encoding such a polypeptide) can be a functional fragment of one of the amino acid sequences described herein. As used herein, a "functional fragment" is a fragment or segment of a peptide which retains at least 50% of the wild-type reference polypeptide's activity according to an assay known in the art or described below herein. For example, a functional fragment described herein would retain at least 50% of the VP1 capsid function. One skilled in the art can assess the function of VP1 using standard techniques, for example those described herein below. A functional fragment can comprise conservative substitutions of the sequences disclosed herein.

In some embodiments, a polypeptide described herein can be a variant of a polypeptide or molecule as described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, e.g., SEQ ID NO: 2, but which has an amino acid sequence different from that of the native or reference polypeptide because of one or a plurality of deletions, insertions or substitutions. A variant capsid polypeptide as the term is used herein retains the capacity for assembly into a viral capsid. Variant polypeptide-encoding DNA sequences encompass sequences that comprise one or more additions, deletions, or substitutions of nucleotides when compared to a native or reference DNA sequence, e.g., SEQ ID NO: 1, but that encode a variant protein or fragment thereof that retains activity of the non-variant polypeptide. A wide variety of PCR-based site-specific mutagenesis approaches are known in the art and can be applied by the ordinarily skilled artisan.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using computer programs commonly employed for this purpose, e.g., that are freely available on the world wide web (e.g. BLASTp or BLASTn with default settings). Alterations of the native amino acid sequence can be accomplished by any of a number of techniques known to one of skill in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of a polypeptide also can be substituted, generally with serine, to improve the oxidative stability of the molecule and prevent aberrant crosslinking. Conversely, cysteine bond(s) can be added to a polypeptide to improve its stability or facilitate oligomerization.

As used herein, the term "DNA" is defined as deoxyribonucleic acid. The term "polynucleotide" is used herein interchangeably with "nucleic acid" to indicate a polymer of nucleosides. Typically, a polynucleotide is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However, the term encompasses molecules comprising nucleosides or nucleoside analogs containing chemically or biologically modified bases, modified backbones, etc., whether or not found in naturally occurring nucleic acids, and such molecules may be preferred for certain applications. Where this specification refers to a polynucleotide it is understood that both DNA, RNA, and in each case both single- and double-stranded forms (and complements of each single-stranded molecule) are provided. "Polynucleotide sequence" as used herein can refer to the polynucleotide material itself and/or to the sequence information (i.e. the succession of letters used as abbreviations for bases) that biochemically characterizes a specific nucleic acid. A polynucleotide sequence presented herein is presented in a 5' to 3' direction unless otherwise indicated.

As used herein, the term "viral vector" refers to a nucleic acid vector construct that includes at least one element of viral origin and has the capacity to be packaged into a viral particle. The viral vector can contain a nucleic acid (e.g., a payload) encoding a polypeptide as described herein in place of non-essential viral genes. The vector and/or particle may be utilized for the purpose of transferring nucleic acids into cells either in vitro or in vivo. Numerous forms of viral vectors are known in the art.

As used herein, an "AAV virus" or "AAV viral particle" refers to a viral particle composed of at least one AAV capsid protein such as VP1 (typically by all of the capsid proteins of a wild-type AAV) and an encapsidated polynucleotide rAAV vector. If the particle comprises a heterologous polynucleotide (i.e. a polynucleotide other than a wild-type AAV genome, such as a transgene to be delivered to a mammalian cell), it is typically referred to as a "recombinant AAV vector particle" or simply a "rAAV vector". Thus, production of a rAAV particle necessarily includes production of a rAAV vector, as such a vector is contained within a rAAV particle.

As used herein, the term "corresponding to," when used in reference to an amino acid or polynucleotide sequence means that a given amino acid or polynucleotide sequence in one polypeptide or polynucleotide molecule has structural properties, functional properties, or both that are similar relative to an amino acid or polynucleotide sequence in a similar location in another polypeptide or polynucleotide molecule. Homologues of a given polypeptide in different species "correspond to" each other, as do regions or domains of homologous polypeptides from different species. Similarly, capsid polypeptides of different serotypes of viral vectors, including but not limited to adeno-associated virus (AAV) vectors, "correspond to" each other, as do regions of such polypeptides, defined, for example by alignment of their amino acid sequences. While other alignment parameters can be used to define such regions, for the avoidance of doubt, alignment can be performed using BLAST® (Basic Local Alignment Search Tool) using default parameters of version BLAST+ 2.8.0 released Mar. 28, 2018.

As used herein, a "transgene" is a polynucleotide encoding a gene that is delivered to a cell by a vector.

A "gene" refers to a polynucleotide containing at least one open reading frame that is capable of encoding a particular gene product after being transcribed, and sometimes also translated. The term "gene" or "coding sequence" refers to a nucleotide sequence in vitro or in vivo that encodes a gene product. In some instances, the gene consists or consists essentially of coding sequence, that is, sequence that encodes the gene product. In other instances, the gene comprises additional, non-coding, sequence that permits, facilitates or directs the cellular expression machinery to express the encoded product. Such sequences can include, but are not limited to promoters, enhancers, transcriptional termination and/or poly(A) addition signals, and elements that affect transcript processing and/or stability. A gene may or may not include regions preceding and following the coding region, e.g. 5' untranslated (5' UTR) or "leader" sequences and 3' UTR or "trailer" sequences, as well as intervening sequences (introns) between individual coding segments (exons).

A "gene product" is a molecule resulting from expression of a particular gene. Gene products include, e.g., a polypeptide, an aptamer, an interfering RNA, an mRNA, and the like. In particular embodiments, a "gene product" is a polypeptide, peptide, protein or interfering RNA including short interfering RNA (siRNA), miRNA or small hairpin RNA (shRNA). In particular embodiments, a gene product is a therapeutic gene product, e.g., a therapeutic protein, or a therapeutic RNA.

As used herein, a "therapeutic gene" refers to a gene that, when expressed, produces a therapeutic gene product that confers a beneficial effect on the cell or tissue in which it is present, or on a mammal in which the gene is expressed. Examples of beneficial effects include amelioration of a sign or symptom of a condition or disease, prevention or inhibition of a condition or disease, or conferral of a desired characteristic. Therapeutic genes include, but are not limited to, genes that correct a genetic deficiency in a cell or mammal.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

SEQUENCE LISTING

The patent contains a lengthy sequence listing. A copy of the sequence listing is available in electronic form from the USPTO web site (https://seqdata.uspto.gov/docdetail?docId=US12617821B2). An electronic copy of the sequence listing will also be available from the USPTO upon request and payment of the fee set forth in 37 CFR 1.19(b)(3).

What is claimed is:

1. A viral capsid polypeptide bearing a mutation relative to SEQ ID NO: 2 (WT AAV2) in a region corresponding to amino acids 561-588, wherein the region corresponding to amino acids 561-588 comprises a sequence selected from SEQ ID NO: 4-41,337.

2. The viral capsid polypeptide of claim 1, which is an AAV capsid polypeptide.

3. The viral capsid polypeptide of claim 2, wherein the AAV capsid polypeptide is an AAV2 capsid polypeptide.

4. The viral capsid polypeptide of claim 1, wherein the viral capsid polypeptide is an AAV VP1 capsid polypeptide.

5. The viral capsid polypeptide of claim 4, wherein the region corresponding to amino acids 561-588 of SEQ ID NO: 2 comprises a sequence selected from SEQ ID NO: 4-41,337.

6. The viral capsid polypeptide of claim 4, which is an AAV2 capsid polypeptide.

7. The viral capsid polypeptide of claim 1, comprising a sequence of SEQ ID NO: 2, wherein the region of amino acids 561-588 of SEQ ID NO: 2 comprises a variant sequence selected from SEQ ID NO: 4-41,337.

8. An AAV2 capsid polypeptide comprising a sequence of SEQ ID NO: 2, wherein the region of amino acids 561-588 of SEQ ID NO: 2 comprises a variant sequence selected from SEQ ID NO: 4-41,337.

9. A nucleic acid encoding the capsid polypeptide of claim 1.

10. An engineered AAV vector having at least a capsid comprising the capsid polypeptide of claim 1.

11. A viral particle comprising the capsid polypeptide of claim 1.

12. A method for delivering a payload, the method comprising contacting a cell with the engineered AAV vector of claim 10.

13. A method for delivering a payload, the method comprising contacting a cell with viral particle of claim 11.

14. The method of claim 13, wherein the contacting is sufficient to allow for expression of the payload in the cell.

15. A method for administering a payload, the method comprising administering to a subject the engineered AAV vector of claim 10.

16. A method for administering a payload, the method comprising administering to a subject the viral particle of claim 11.

17. The method of claim 16, wherein the administering is sufficient to allow for expression of the payload in the cell.

18. The method of claim 16, wherein the payload is selected from the group consisting of: a nucleic acid, a polypeptide, an inhibitory RNA, an antibody or antibody reagent, an oligonucleotide, and a miRNA.

\* \* \* \* \*